United States Patent [19]

Bradshaw

[11] Patent Number: 4,595,878
[45] Date of Patent: Jun. 17, 1986

[54] NMR MEASUREMENT ON FROZEN CORES

[75] Inventor: Gale T. Bradshaw, Norman, Okla.

[73] Assignee: Standard Oil Company (Indiana), Chicago, Ill.

[21] Appl. No.: 645,932

[22] Filed: Aug. 29, 1984

Related U.S. Application Data

[63] Continuation-in-part of Ser. No. 418,353, Sep. 15, 1982, abandoned.

[51] Int. Cl.⁴ ............................................. G01R 33/20
[52] U.S. Cl. ..................................... 324/300; 324/303
[58] Field of Search ............... 324/300, 303, 307, 362, 324/366; 73/152, 153

[56] References Cited

U.S. PATENT DOCUMENTS

| | | | |
|---|---|---|---|
| 2,913,658 | 11/1959 | Burdine | 324/318 |
| 3,987,361 | 10/1976 | Martin | 324/300 |
| 4,291,271 | 9/1981 | Lauffer | 324/307 |
| 4,295,365 | 10/1981 | Meshri | 324/307 |
| 4,350,955 | 9/1982 | Jackson et al. | 324/303 |

OTHER PUBLICATIONS

S. C. Mraw et al., "Water in Coal Pores: Low Temperature Heat Capacity Behavior of the Moisture of Wyodak Coal," Science, vol. 205, Aug. 1979, pp. 901, 902.

Primary Examiner—Michael J. Tokar

[57] ABSTRACT

A method of evaluating geologic rock samples and particularly sandstone. The sample is saturated with fresh water and the temperature of the sample is reduced to a temperature below the freezing point of the fresh water. As the sample is warmed, nuclear magnetic resonance measurements are made at just below 0° C. and again at about the operating temperature of the NMR probe, i.e., about 32° C. The portion of the water within the sample that can be considered to be residual water can be determined from the relationship of NMR measurements taken at just below 0° C. and at the temperature of the probe.

15 Claims, 4 Drawing Figures

NMR MEASUREMENT ON FROZEN CORES

This application is a continuation-in-part of application Ser. No. 418,353 filed Sept. 15, 1982, now abandoned.

BACKGROUND OF THE INVENTION

1. Field of the Invention

This invention relates to the analysis of rocks and particularly core samples cut from subterranean sandstone formations with a nuclear magnetic resonance measuring instrument for determining the percent of the pore space that is occupied by residual water.

2. Setting of the Invention

In drilling holes in the earth for the production of oil and gas, it is common practice to obtain core samples of the subterranean formation through which the hole is drilled. These cores, as well as providing visual information as to the nature of the subterranean formation, can be analyzed to obtain important physical parameters such as porosity, permeability, fluid content, and the rock type of the formation from which the sample is cut. All rock samples taken from petroleum bearing subterranean formations contain in addition to the hydrocarbon at least a small amount of water. One important characteristic of the core sample which the petroleum engineer or geologist needs to ascertain is the percent of the pore space of the subterranean formation which is occupied by residual water. This determination of residual water can provide an indication of whether hydrocarbon production is possible in an economically viable manner. By residual water, what is meant is that water within the subterranean formation which will not flow when the pressure on the formation is reduced, such as during production through a borehole penetrating the subterranean formation. A portion of the residual water is adsorbed or otherwise bound to the internal surfaces of the subterranean formation and a portion is contained within small pore spaces. The capillary forces holding the water within the small pore spaces is too great to be overcome by the reduced pressure during production. The majority of the residual water is usually contained within the smaller pore spaces of the subterranean formation.

SUMMARY OF THE INVENTION

This invention concerns a method of analyzing a geologic sample taken from a subterranean sandstone formation. From a nuclear magnetic resonance (NMR) measurement made under conditions such that substantially all of the water in the larger pore spaces of the sample will be in the solid state and an NMR measurement with substantially all of such water being in the liquid state, it is possible to determine a measure of the residual water saturation of the sample.

In one embodiment for carrying out this invention, a rock sample is treated for removing hydrocarbons and aqueous liquids from the sample and then the sample is saturated with fresh water. The rock sample is then cooled to a temperature below 0° C. and placed in a nuclear magnetic resonance measuring instrument. A nuclear magnetic resonance measurement is made on the rock sample at a temperature of about the freezing temperature of the fresh water but under conditions such that it would be expected that substantially all of the water within the larger pore spaces of the rock sample is in the solid state. A second nuclear magnetic resonance measurement is made on the rock sample under conditions such that it would be expected that substantially all of the water in the larger pore spaces of the rock sample is in the liquid state. These measurements are used for determining the residual water content of the rock sample. The ratio of the NMR measurement with substantially all of the water being in the solid state and the NMR measurement with substantially all of the water being in the liquid state has been determined to represent the ratio of the residual water content of the rock sample to the total water content of the saturated rock sample.

DETAILED DESCRIPTION OF THE INVENTION

It was determined, while analyzing nuclear magnetic resonance (NMR) measurements of frozen sandstone samples that the water within the pores of the samples does not all freeze at the same temperature. Additionally, it was determined from NMR measurements that some of the water within the sandstone rock samples remains unfrozen even when the temperature of the samples are lowered and allowed to equilibrate at temperatures as low as about −40° C. It is thought that the forces involved in the adsorption of water to the surfaces within the sample can keep a portion of the water from freezing and that a portion of the water is in such small pore spaces that ice crystal formation is inhibited. It is also thought that the water adsorbed on the surface within the sample and the water within these small pore spaces will not be produced when the pressure on the formation from which the sample was taken is reduced. Therefore, in accordance with this invention it has been discovered that the amount of unfrozen water at just below 0° C. can be determined from NMR measurements and that this can be used for determining the residual water content of sandstone formations.

Figure 1:
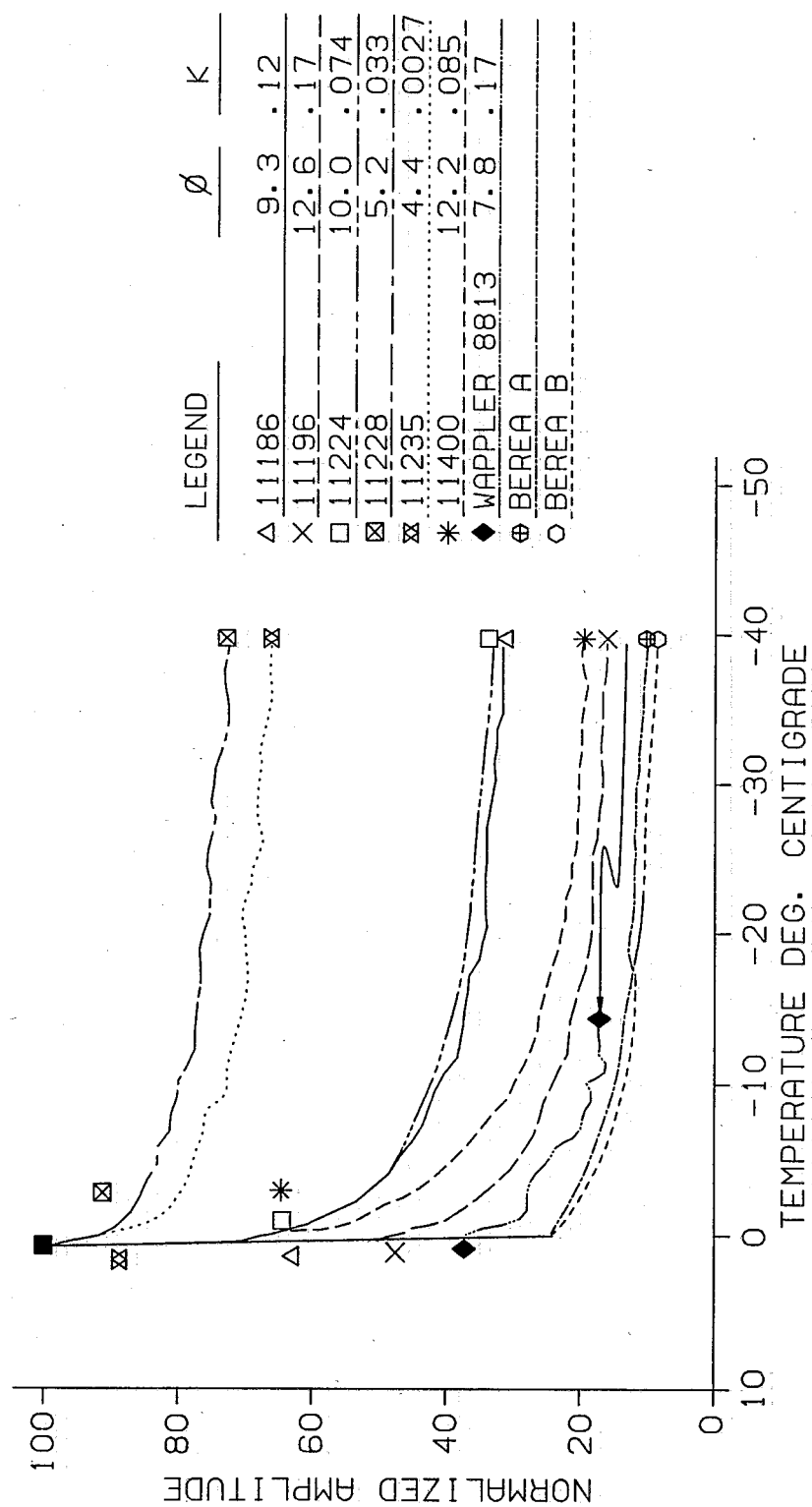
FIG. 1 is a plot of temperature versus normalized NMR amplitude for various samples of sandstone as the samples warm from −40° C. to 0° C.

FIG. 1 shows plots of temperature versus normalized NMR amplitude for several samples of sandstone as the temperature of the samples increased from about −40° C. to about 0° C.

Any NMR instrument capable of making the measurements that must be made can be used. A Praxis 103 NMR instrument which is commercially available from Praxis, San Antonio, Tex., was used in making the measurements from which the data presented herein were obtained. This instrument was modified by adding Styrofoam insulation, with a thickness of 2.4 mm inside the coil of the NMR instrument to thermally insulate the sample. Insulation with a thickness of 4.8 mm was also added to the bottom of the probe of the NMR instrument. The term "probe" means the part of the NMR instrument between the magnetic poles inside the instrument and containing the coil into which the sample is inserted. Various insulation schemes can be used as long as there is no detuning of either the coil or the magnet of the NMR instrument. The shape of the rock samples used for making these measurements was cylindrical with dimensions of approximately ¾ in. in diameter and 1 in. in length. In further preparation of the rock samples, a hole 0.1 in. in diameter was drilled 0.4 in. deep into the center of one end of the samples to provide a temperature measuring point near the center of the samples. An Omega Model 199 digital readout temperature measuring device which is commercially available from Omega Engineering, Inc., Stanford, Conn., with 1° C. resolution was used to monitor the temperature within the hole in the samples. Copper-constantan thermocouples which are also commercially available from Omega Engineering, Inc., were used for making the temperature measurements. These thermocouples are nonmagnetic and do not detune the NMR probe.

Prior to making the NMR measurements, the rock samples were treated to remove fluids, such as hydrocarbons and aqueous fluids, from the pore spaces of the samples and then the samples were saturated with fresh water. After saturation of the rock samples with the fresh water, the samples were placed in powdered dry ice and cooled to about the temperature of the dry ice, e.g., about −40° C. The samples were individually removed from the dry ice and immediately placed in the NMR instrument which was in a laboratory room which had a temperature of about 70°–80° F. or about 25° C. NMR measurements were made as the temperature of the rock samples increased from about −40° C. to about 0° C. and then at the temperature of the NMR probe which was about 90° F. or 32° C. Suitable fresh water for saturating the samples is any aqueous liquid that does not have a concentration of material dissolved therein that would affect its freezing characteristics.

At temperatures below about 0° C. it is thought that a portion of the NMR measurement is due to the protons associated with ice and the mineral structure of the rock samples and that a portion of the measurement is due to protons associated with water in the liquid state. Therefore, periodically as the sample warmed up, the amplitude of the free induction signal following a 90° pulse and a delay to allow the ice signal to decay and the sample temperatures were measured and recorded. The "ice signal" is a short signal that occurs first after the 90° pulse. The ice signal varies in duration in response to the temperature and particular NMR instrument and may last up to about 90 microseconds. The part of the NMR measurement representing response to water in a liquid state immediately follows the ice signal. It is this response to water in a liquid state that is of primary interest and which was measured and recorded.

The results of these NMR measurements are illustrated on FIG. 1, with a plot of temperature on the abscissa versus normalized NMR amplitude on the ordinate for each of the nine samples. The samples indicated by legends 11186, 11196, 11224, 11228, 11235 and 11400 were sandstone samples taken from a well at approximately the depths indicated by these numbers. The sandstone samples indicated by legend Wappler 8813 was taken from another well. Samples indicated by legends Berea A and Berea B are sandstone samples taken from well known rock outcrops in Illinois. It should be noted that the term "normalized NMR amplitude" in FIG. 1 refers to the recorded NMR amplitude at the corresponding temperature divided by the recorded NMR amplitude of the sample at 90 F. and with all of the water in the sample unfrozen, and multiplied by 100.

The purpose for normalizing NMR amplitude in this way is to provide a measure of the relationship between actual NMR amplitude which was measured and the actual NMR amplitude which was measured at a temperature where it would be expected that substantially all of the water in the sample that is saturated with fresh water will be completely unfrozen. It should be noted that since the actual amplitude of an NMR signal which was measured under conditions where it would be expected that substantially all of the water in the pore spaces is in its liquid state at the time the NMR amplitude was measured will be a function of the amount of water present in the sample that is saturated with fresh water and hence the pore space of the sample. The normalized NMR amplitude also has the effect of removing porosity as a variable affecting NMR amplitude.

It can be seen in FIG. 1, that normalized amplitude exists at temperatures as low as −40° C. Since the ice signal has been filtered out, the reading indicates the presence of unfrozen water. As previously discussed, this liquid water is thought to be present in small pores or adsorbed onto the rock surface of the pores. As the temperature slowly increases from −40° C. the normalized amplitude increases. This is thought to be due to melting of water in the smaller pores, where freezing occurred somewhere between 0° C. and −40° C. This water, however, is still thought to be residual. From Equation 1 below, as found in "Calorimetric Evidence for the Capillary Condensation Theory" by Szumi Higuti and Yashihomo Iwagani at page 921, Volume 56, Journal of Physical Chemistry, 1952, the pore size distribution can be obtained. For a given normalized amplitude or the percentage of water unfrozen at a given temperature below 0° C. the same percentage of pores must have an average radius of not over "r" in Equation 1:

$$r = \frac{12.4 \times 10^{-6} \text{ cm}}{\Delta T} \quad (1)$$

where $\Delta T$ is the temperature of the sample in degrees centigrade below 0° C.

As an example of this, for sample 11196, when the probe had a temperature of −5° C., the normalized amplitude for the sample was approximately 30. Utilizing Equation 1, it can be calculated that 30% of the pores had an average radius of not over $2.5 \times 10^{-6}$ cm. It is thought that this pore radius would be so small that water would not flow from these pores during production. It is seen, for example from the plot of normalized NMR amplitude versus temperature for Sample 11196 on FIG. 1, that normalized NMR amplitude increases substantially between about −5° C. and just below 0° C. A calculation of the average radius of pore sizes below which water would be in an unfrozen state at −1° C. ($12.4 \times 10^{-6}$ cm), −0.3° C. ($41.3 \times 10^{-6}$ cm) and −0.1° C. ($124 \times 10^{-6}$ cm) show that the average radius of pores containing unfrozen water also increases substantially as the temperature increases from −5° C. to −0.1° C. It is thought that water will not be produced from pores that have radii of less than about $10 \times 10^{-6}$ cm and possibly from pores that have radii of less than about $50 \times 10^{-6}$ cm. As seen from these discussions, normalized NMR amplitudes measured at temperatures above about $-1°$ C. and possibly above about $-0.3°$ C. may include an NMR response from liquid water other than residual water.

It can further be seen on FIG. 1, that at the temperature of 0° C., as the sample completely thaws, the normalized amplitude increases to a value of 100. The NMR normalized amplitude at the time the sample first warms to just less than 0° C. is a measurement of water unfrozen in the sample due to some feature of the sample. It is thought that the unfrozen water is adsorbed to the surface within the sample or contained in such small pores that it will not be produced. It is therefore considered that normalized NMR amplitudes as the sample first warms to just less than 0° C. are a measurement of the residual water saturation of the sample.

Figure 2:
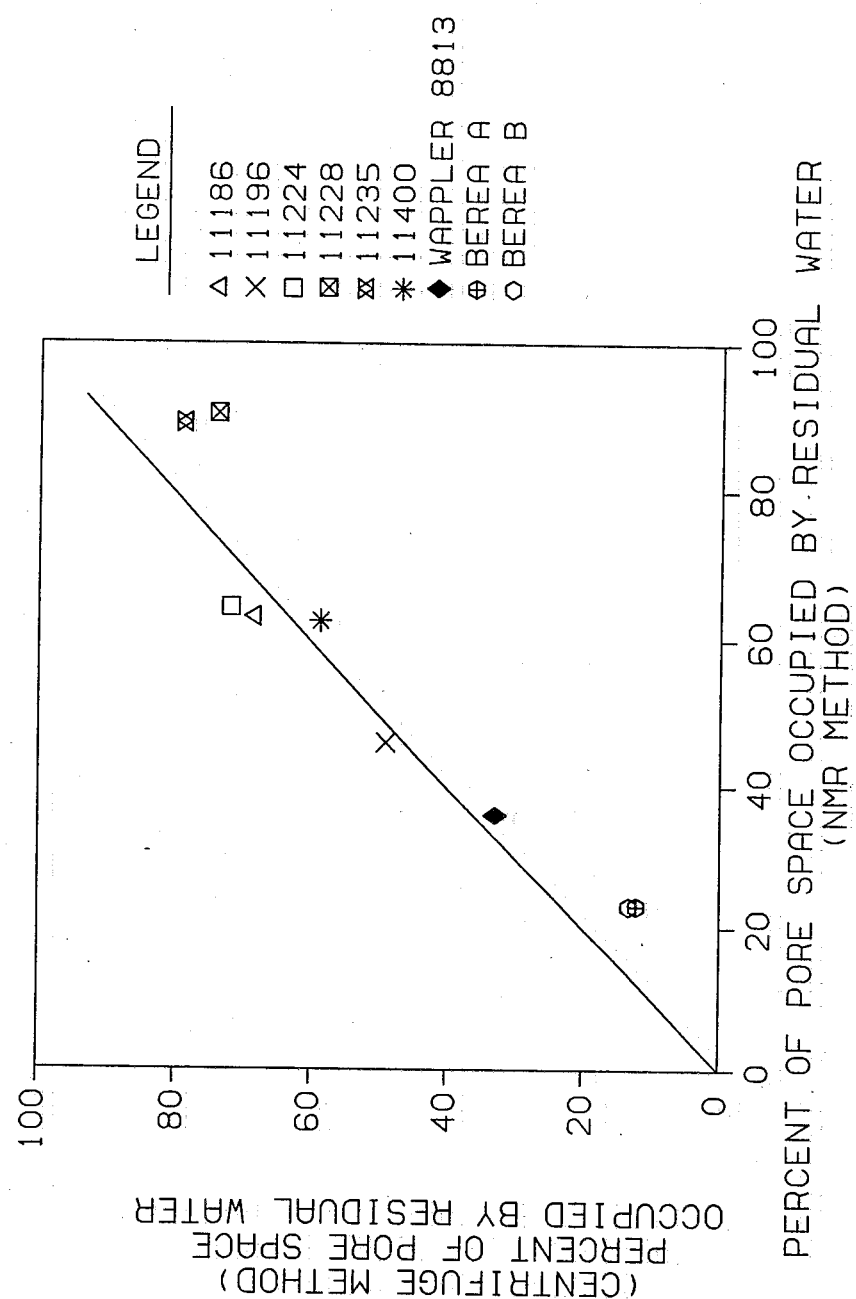
FIG. 2 shows the correlation between the residual water content of the sandstone samples identified in regard to FIG. 1 as determined by the NMR method of this invention and a centrifuge method.
Figure 3:
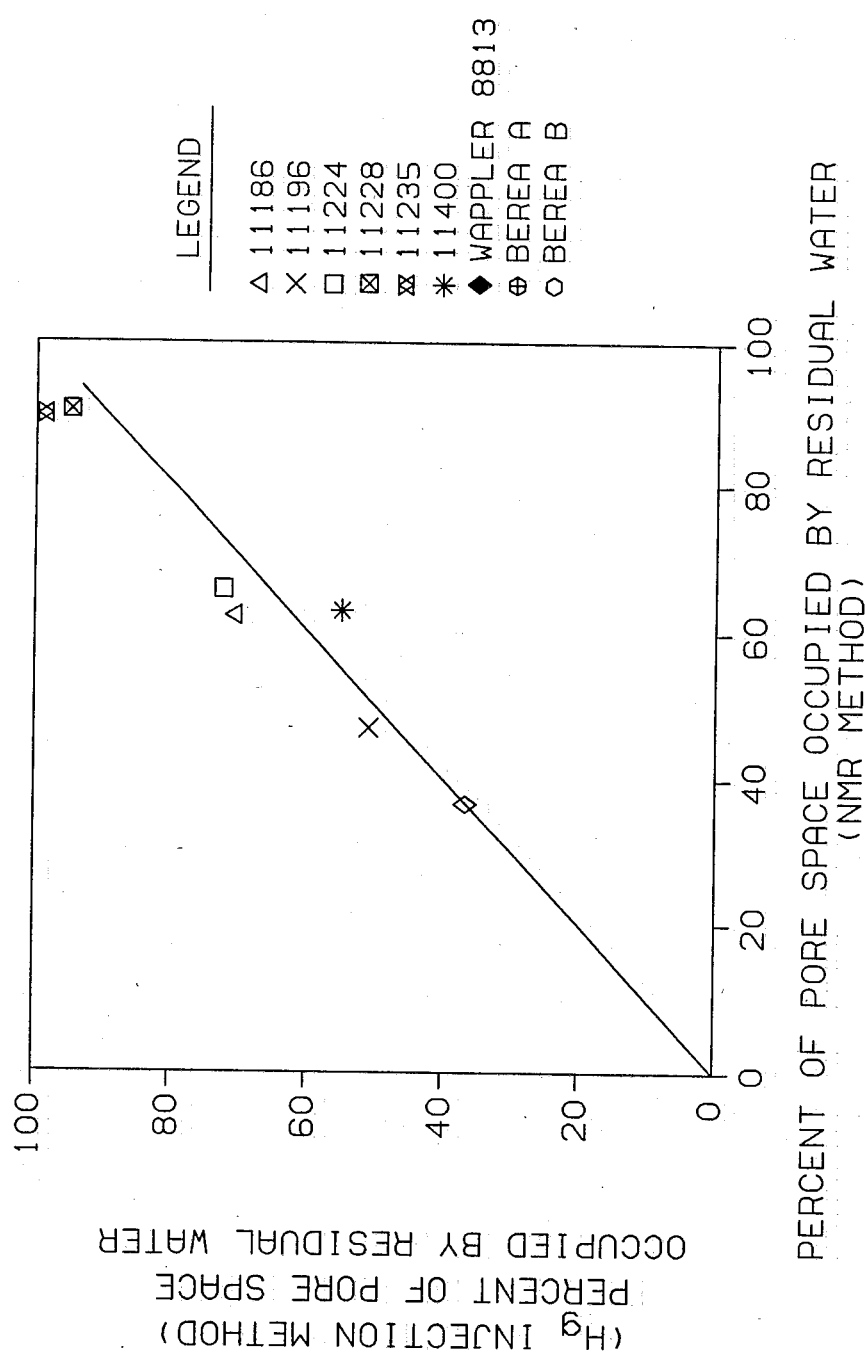
FIG. 3 shows the correlation between the residual water content of the sandstone samples identified in regard to FIG. 1 as determined by the NMR method of this invention and a mercury injection method.
Figure 4:
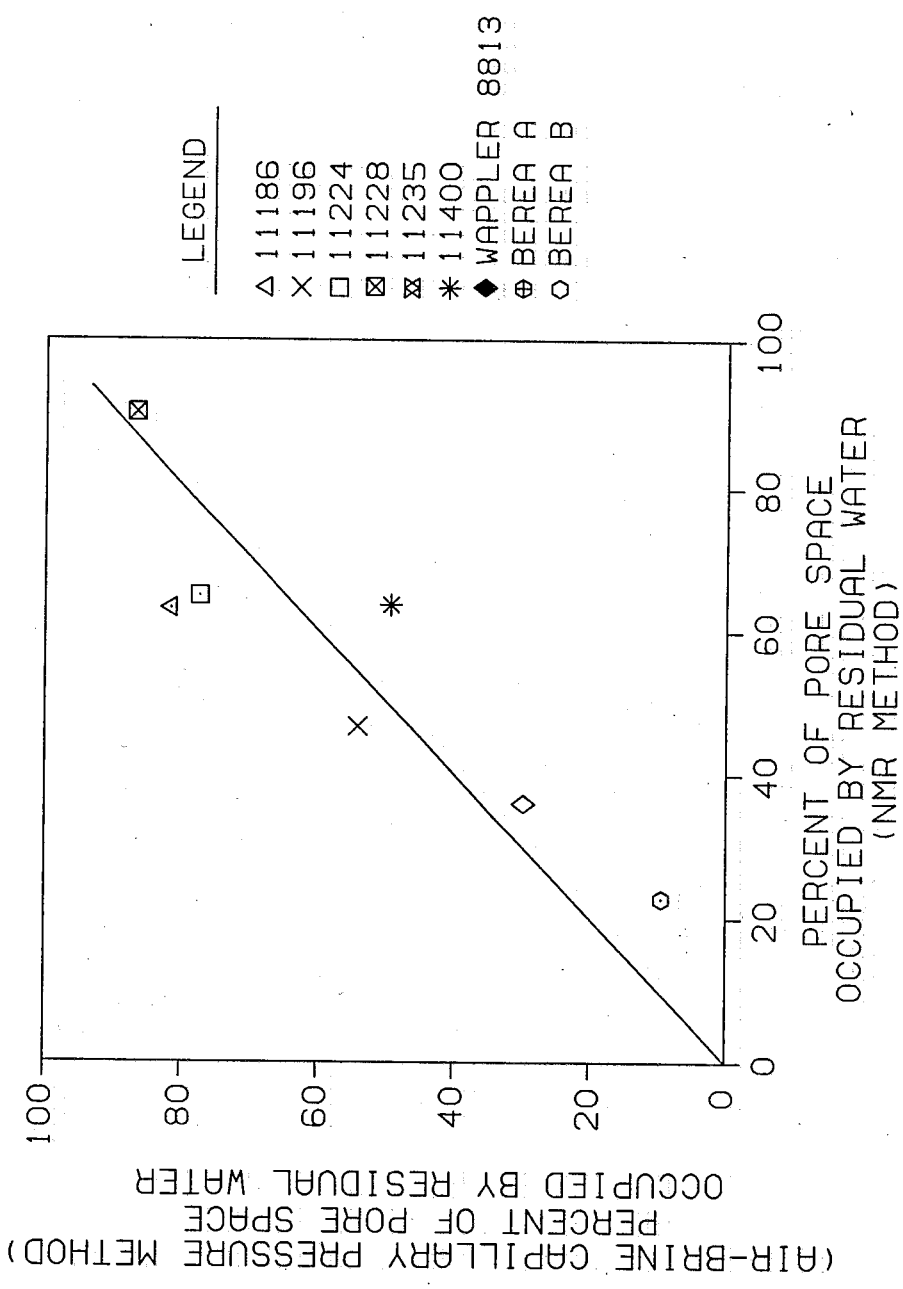
FIG. 4 shows the correlation between the residual water content of the sandstone samples identified in regard to FIG. 1 as determined by the NMR method of this invention and an air-brine capillary pressure method.

This interpretation finds support in FIGS. 2, 3, and 4 which show the correlation between the percent of the pore space of samples which are occupied by residual water as determined by the NMR method of this invention and three commercially recognized methods for making residual water determinations. The samples used in FIG. 1 were also used in FIGS. 2, 3, and 4 and the legends indicated thereon are consistent.

In relation to FIG. 2, water saturation was determined by a commercially recognized centrifuge method for each rock sample by weighing the sample prior to saturating it with fresh water, weighing the sample while 100% water saturated and then reweighing the sample after centrifuging the sample at 10,000 RPM's for 20 min. These conditions were chosen arbitrarily but it is thought that these conditions would ensure that only the residual water is left in the sample. An equal value line drawn at 45° to the abscissa of FIG. 2 shows that there is a good correlation between the percent of the pore space occupied by residual water as determined by the NMR method of this invention and the centrifuge method of determining the residual water content of samples.

In FIG. 3, the water saturation was determined by a commercially recognized mercury injection method. FIG. 3 shows that there is a good correlation between the percent of pore space occupied by residual water as determined by the NMR method of this invention and this mercury injection method of determining the residual water content of samples. In FIG. 4 the water saturation was determined by a commercially recognized air-brine capillary pressure method. FIG. 4 shows that there is a good correlation between the percent of pore space occupied by residual water as determined by the NMR method of this invention and this air-brine method of determining the residual water content of samples.

The water saturation determined by these three methods correlates very closely with the percent of pore space occupied by residual water as determined by the NMR method of this invention and represented by the normalized NMR amplitude at just below 0° C. Thus, the NMR technique defined here can be used as a measure of the residual water saturation of sandstone samples in that the percent of residual water in a sample is equal to the normalized NMR reading when the sample is cooled to a temperature below 0° C. and then first warms to just below 0° C. in comparison to the NMR readings when substantially all of the water in the core is in its liquid state.

All of the above description has been made in great detail, various modifications can be made therein without departing from the spirit or scope of the invention.

What is claimed is:

1. A method of analyzing a geological sample taken from a subterranean formation and saturated with fresh water which comprises:
   (a) making a nuclear magnetic resonance (NMR) measurement of said sample with said sample at just below the freezing temperature of the fresh water to obtain a first value,
   (b) making an NMR measurement on said sample with said sample and the fresh water therein being above the freezing temperature of the fresh water to obtain a second value,
   (c) obtaining a ratio of said first and second values.

2. A method of analyzing a geological sandstone sample taken from a subterranean formation which comprises:
   (a) treating said sample for removing fluids from said sample and saturating said sample with fresh water,
   (b) lowering the temperature of said sample until the sample is completely below the freezing temperature of fresh water,
   (c) running a nuclear magnetic resonance (NMR) measurement on said sample as it warms to just below 0° C.,
   (d) obtaining the NMR measurement when the temperature of the sample is completely raised to above the melting temperature of fresh water,
   (e) obtaining the residual water saturation value by dividing the value obtained in Step (c) by that obtained in Step (d).

3. The method as defined in claim 2 in which in Step (b) the sample is lowered to a temperature of approximately $-40°$ C.

4. A method of analyzing a subterranean core containing water comprising:
   (a) lowering the temperature of a core below the freezing point of water,
   (b) running nuclear magnetic resonance measurements on said core during the time its temperature rises from the temperature in Step (a) to a temperature so that all of the water in the core is thawed.

5. A method as defined in claim 4 in which the temperature of the core is lowered to at least $-40°$ C.

6. A method as defined in claim 4 in which the temperature determined in Step (b) is plotted as the abscissa and the NMR measurement as the ordinate.

7. A method for determining pore size distribution of a rock sample which comprises:
   (a) determining the normalized NMR amplitude of a rock sample at a selected temperature below 0° C.,
   (b) determining the average pore radius (r) at the selected temperature from the equation $$r = \frac{12.4 \times 10^{-6} \text{ cm}}{\Delta T} \quad (2)$$

where $\Delta T$ = numerical representation of the selected temperature in °C. below 0° C.,
   (c) utilizing the normalized NMR amplitude as determined from Step (a) for determining the percentage of pores within the rock sample having an average pore radius of not greater than the pore radius determined in Step (b).

8. A method of determining the residual water content of a rock sample from a subterranean formation, comprising:

treating the rock sample for removing fluids from the rock sample and then saturating the rock sample with fresh water, making nuclear magnetic resonance measurements on the saturated rock sample which is at a first temperature of about the freezing temperature of the fresh water and under conditions wherein it would be expected that substantially all of the fresh water within the larger pore spaces of the rock sample will be in its solid state and at a second temperature wherein it would be expected that substantially all of the fresh water in the larger pore spaces of the rock sample will be in its liquid state and, using the measurements taken at the first and second temperatures in determining the residual water content of the rock sample.

9. A method as defined in claim 8 wherein the first temperature is about $-1°$ C.

10. A method as defined in claim 8 wherein the first temperature is within the range of about $-0.3°$ C. to $-1°$ C.

11. A method as defined in claim 8 wherein the second temperature is about room temperature.

12. A method as defined in claim 8 wherein the second temperature is about $32°$ C.

13. A method as defined in claim 8 wherein the ratio of the measurements at the first and second temperatures is considered to be the ratio of residual water content of the rock sample to the total water content of the saturated rock sample.

14. A method as defined in claim 8 wherein the measurements of the portion of the NMR signal associated with water in its liquid state is used in determining the residual water content of the rock sample.

15. A method as defined in claim 8 wherein the rock sample is sandstone.

* * * * *